US009632039B2

(12) United States Patent
Den Boef et al.

(10) Patent No.: US 9,632,039 B2
(45) Date of Patent: Apr. 25, 2017

(54) INSPECTION APPARATUS, INSPECTION METHOD AND MANUFACTURING METHOD

(71) Applicants: Vrije Universiteit Amsterdam, Amsterdam (NL); Universiteit van Amsterdam, Amsterdam (NL); Stichting voor Fundamenteel Onderzoek der Materie, Utrecht (NL); ASML Netherlands B.V., Veldhoven (NL)

(72) Inventors: Arie Jeffrey Den Boef, Waalre (NL); Simon Gijsbert Josephus Mathijssen, Rosmalen (NL); Nitesh Pandey, Eindhoven (NL); Stefan Michiel Witte, Hoofddorp (NL); Kjeld Eikema, Amsterdam (NL)

(73) Assignee: ASML Netherlands B.V., Veldhoven (NL)

( * ) Notice: Subject to any disclaimer, the term of this patent is extended or adjusted under 35 U.S.C. 154(b) by 40 days.

(21) Appl. No.: 14/838,268

(22) Filed: Aug. 27, 2015

(65) Prior Publication Data
US 2016/0061750 A1    Mar. 3, 2016

(30) Foreign Application Priority Data
Aug. 28, 2014 (EP) ..................... 14182658

(51) Int. Cl.
*G03B 27/54*    (2006.01)
*G01N 21/956*   (2006.01)
(Continued)

(52) U.S. Cl.
CPC ........... *G01N 21/956* (2013.01); *G01B 11/00* (2013.01); *G03F 7/70141* (2013.01);
(Continued)

(58) Field of Classification Search
CPC ................. G03F 7/70625; G03F 7/70633
(Continued)

(56) References Cited

U.S. PATENT DOCUMENTS

2006/0033921 A1    2/2006    Den Boef et al.
2006/0066855 A1    3/2006    Boef et al.
(Continued)

FOREIGN PATENT DOCUMENTS

TW    201226891 A    7/2012
TW    201333432 A    8/2013
(Continued)

OTHER PUBLICATIONS

International Search Report directed to App. No. PCT/EP2015/068702, mailed Nov. 26, 2015; 4 pages.
(Continued)

*Primary Examiner* — Hung H Nguyen
(74) *Attorney, Agent, or Firm* — Sterne, Kessler, Goldstein & Fox P.L.L.C.

(57) ABSTRACT

Metrology targets are formed on a substrate (W) by a lithographic process. A target (T) comprising one or more grating structures is illuminated with spatially coherent radiation under different conditions. Radiation (650) diffracted by from said target area interferes with reference radiation (652) interferes with to form an interference pattern at an image detector (623). One or more images of said interference pattern are captured. From the captured image (s) and from knowledge of the reference radiation a complex field of the collected scattered radiation at the detector. A synthetic radiometric image (814) of radiation diffracted by each grating is calculated from the complex field. From the synthetic radiometric images (814, 814') of opposite portions of a diffractions spectrum of the grating, a measure of asymmetry in the grating is obtained. Using suitable targets,
(Continued)

overlay and other performance parameters of the lithographic process can be calculated from the measured asymmetry.

19 Claims, 4 Drawing Sheets

(51) Int. Cl.
  *G03F 7/20* (2006.01)
  *G01B 11/00* (2006.01)
  *G03H 1/04* (2006.01)
  *G03H 1/00* (2006.01)
  *G03H 1/02* (2006.01)
(52) U.S. Cl.
  CPC ...... *G03F 7/70625* (2013.01); *G03F 7/70633* (2013.01); *G03F 7/70641* (2013.01); *G03H 1/0443* (2013.01); *G01N 2201/12* (2013.01); *G03H 2001/0033* (2013.01); *G03H 2001/0204* (2013.01); *G03H 2001/0458* (2013.01)
(58) Field of Classification Search
  USPC .......................... 355/52, 53, 55, 67; 356/372
  See application file for complete search history.

(56) References Cited

U.S. PATENT DOCUMENTS

| | | |
|---|---|---|
| 2008/0095312 A1 | 4/2008 | Rodenburg et al. |
| 2010/0201963 A1 | 8/2010 | Cramer et al. |
| 2010/0241396 A1 | 9/2010 | Rodenburg |
| 2011/0001970 A1 | 1/2011 | Maiden |
| 2011/0027704 A1 | 2/2011 | Cramer et al. |
| 2011/0043791 A1 | 2/2011 | Smilde et al. |
| 2011/0102753 A1 | 5/2011 | Van De Kerkhof et al. |
| 2011/0235862 A1 | 9/2011 | Roberts et al. |
| 2012/0044470 A1 | 2/2012 | Smilde et al. |
| 2012/0081684 A1 | 4/2012 | Den Boef et al. |
| 2012/0105744 A1 | 5/2012 | Maiden |
| 2012/0123581 A1 | 5/2012 | Smilde et al. |
| 2013/0033703 A1 | 2/2013 | Humphry et al. |
| 2013/0181990 A1 | 7/2013 | Rodenburg et al. |
| 2013/0223685 A1 | 8/2013 | Maiden |
| 2013/0258310 A1 | 10/2013 | Smilde et al. |
| 2013/0271740 A1 | 10/2013 | Quintanilha |
| 2014/0111791 A1 | 4/2014 | Manassen et al. |

FOREIGN PATENT DOCUMENTS

| | | |
|---|---|---|
| WO | WO 2009/078708 A1 | 6/2009 |
| WO | WO 2009/106279 A1 | 9/2009 |
| WO | WO 2013/143723 A1 | 10/2013 |
| WO | WO 2013/178422 A1 | 12/2013 |
| WO | WO 2014/035238 A1 | 3/2014 |

OTHER PUBLICATIONS

Yamaguchi, I., et al., "Phase Shifting Digital Holography," Optics Letters, Optical Society of America, vol. 22, No. 16, Aug. 15, 1997; pp. 1268-1270.
English-language Abstract of Taiwanese Patent Publication No. TW201226891 A, published Jul. 1, 2012; 2 pages.
English-language Abstract of Taiwanese Patent Publication No. TW201333432 A, published Aug. 16, 2013; 1 page.
2007 Research Summary, Abstracts for Ming C. Wu, UC Berkeley College of Engineering, last updated Nov. 2, 2015, accessed at https://buffy.eecs.berkeley.edu/PHP/resabs/resabs.php?f_year=2007&f_submit=advgrp&f_advid=11730277; 10 pages.
"Digital holography," Wikipedia—The Free Encyclopedia, accessed http://en.wikipedia.org/wiki/Digital_holography on Jul. 29, 2014; 4 pages.
"Frequency-resolved optical gating," Wikipedia—The Free Encyclopedia, accessed at http://en.wikipedia.org/wiki/Frequency-resolved_optical_gating on Jul. 23, 2014; 4 pages.
Gross, D., et al., "Phase Focus: Take a Closer Look," Equity Development, Dec. 10, 2010; 27 pages.
Mann, P., "Intel takes the next step in Silicon Photonics," HEXUS. net, dated Jul. 27, 2010, accessed at http://hexus.net/tech/news/mainboard/25707-intel-takes-next-step-silicon-photonics; 3 pages.
"Spectral phase interferometry for direct electric-field reconstruction," Wikipedia—The Free Encyclopedia, accessed at https://en.wikipedia.org/wiki/Spectral_phase_interferometry_for_direct_electric-field_reconstruction on Jul. 23, 2014; 4 pages.
Wyant, J.C., "Phase-Shifting Interferometry," The University of Arizona College of Optical Sciences, Optics 513 Optical Testing, Chapter 5 Notes, 2011; 35 pages.

INSPECTION APPARATUS, INSPECTION METHOD AND MANUFACTURING METHOD

BACKGROUND

Field of the Invention

The present invention relates to inspection apparatus and methods usable, for example, to perform metrology in the manufacture of devices by lithographic techniques. The invention further relates to an illumination system for use in such inspection apparatus and to methods of manufacturing devices using lithographic techniques. The invention yet further relates to computer program products for use in implementing such methods.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a diffraction "spectrum" from which a property of interest of the target can be determined.

Examples of known scatterometers include angle-resolved scatterometers of the type described in US2006033921A1 and US2010201963A1. The targets used by such scatterometers are relatively large, e.g., 40 μm by 40 μm, gratings and the measurement beam generates a spot that is smaller than the grating (i.e., the grating is underfilled). In addition to measurement of feature shapes by reconstruction, diffraction based overlay can be measured using such apparatus, as described in published patent application US2006066855A1. Diffraction-based overlay metrology using dark-field imaging of the diffraction orders enables overlay measurements on smaller targets. Examples of dark field imaging metrology can be found in international patent applications WO 2009/078708 and WO 2009/106279 which documents are hereby incorporated by reference in their entirety. Further developments of the technique have been described in published patent publications US20110027704A, US20110043791A, US20111102753A1, US20120044470A, US20120123581A, US20130258310A, US20130271740A and WO2013178422A1. These targets can be smaller than the illumination spot and may be surrounded by product structures on a wafer. Multiple gratings can be measured in one image, using a composite grating target. The contents of all these applications are also incorporated herein by reference.

The inspection apparatus that will be used as a metrology tool in such an environment should meet many requirements. Realizing these requirements typically involves significant compromises. For example, high-NA broadband optics with low aberrations leads to many lens elements usually composed of different materials. Each of these elements contributes to internal scattering which limits the detectability of weak targets. Also it becomes increasingly more difficult to have good anti-reflection coatings over a large wavelength range. Having so many optical components leads to an apparatus that is difficult to adjust properly for the metrology application.

SUMMARY OF THE INVENTION

The present invention aims to provide an alternative inspection apparatus and method for performing measurements of the type described above.

According to a first aspect of the present invention, there is provided an inspection apparatus for measuring properties of a target structure, the apparatus comprising a radiation source and an image detector in combination with an optical system, the optical system defining the following beam paths:

an illumination path for receiving radiation from the radiation source, forming a beam of spatially coherent illuminating radiation and delivering said illuminating radiation onto a target area on a substrate;

a collection path for collecting at least a portion of non-zero order scattered radiation from said target area and delivering the collected scattered radiation to the image detector; and a reference path for delivering reference radiation to the image detector, wherein the reference radiation is coherent with the scattered radiation so as to interfere with the scattered radiation and form an interference pattern at the image detector, wherein the image detector is configured to capture one or more images of said interference pattern, and wherein the inspection apparatus further comprises a processor arranged (i) to receive image data representing said one or more captured images, (ii) to calculate from the image data and from knowledge of the reference radiation a complex field of the scattered radiation at the detector, (iii) to calculate from the complex field a synthetic radiometric image of radiation diffracted by a periodic structure within the target area.

Such an apparatus can be used to perform so-called "lensless" imaging. This avoids the difficulties associated with the complex broadband, high-NA objective. The image obtained and used to measure properties of the target is called a "synthetic image" because it never existed in the physical world: it exists only as data and is obtained by computation from data representing the complex field. The calculation of the complex field and then the calculation of the synthetic image can be designed to simulate the processing of radiation that one would wish to be performed in an ideal physical optical system. The advantage is that such an ideal physical optical system cannot be achieved in the physical world, while in the computational world it can. While the system may be referred to as "lensless", this does not exclude the inclusion of one or more optical elements for example for collimation, magnification. What is significant is that the quality of the synthetic images no longer depends on the quality of the optical components.

"Radiometric" imaging means making an image that represents quantitatively the intensity, amplitude and/or phase of the scattered radiation as a function of direction. In the present application, radiometric imaging is used to create an image of the spatial variation of the diffraction efficiency of periodic structures. In the example of small target diffraction based metrology, these structures may be small gratings. In the present application we collect scattered/diffracted light in an image, and compute the desired radiometric image from this scattered light. The image sensor may be located close to the target area so as to collect radiation at a wide range of different angles.

The "structure" within the target area can be arbitrary. However, in applications of interest in the present disclosure, it will be understood that structure within the target area may comprise one or more target structures whose properties are of interest for monitoring the performance of a lithographic process. "Diffraction efficiency" of the structure refers to the proportion of the illuminating radiation that is emitted in a given direction. In the case of a periodic structure within the target area, diffraction efficiency can be measured for each diffraction order, within the range of angles captured by the detector.

In embodiments suitable for measuring performance parameters such as overlay, focus or dose, the processor may be further arranged (iv) to repeat steps (i) to (iii) under different conditions and calculate at least one further synthetic radiometric image of the same target area and (v) to calculate from the plurality of synthetic radiometric images a measure of asymmetry in the target structure The invention further provides a method for measuring properties of a target structure, the method comprising the steps:

(a) illuminating a target area on a substrate with spatially coherent illuminating radiation;
(b) collecting at least a portion of non-zero order scattered radiation from said target area and delivering the collected scattered radiation to the image detector;
(c) delivering a beam of reference radiation to the image detector the reference radiation being coherent with the scattered radiation so as to interfere with the collected scattered radiation and form an interference pattern at the image detector;
(d) capturing with the image detector one or more images of said interference pattern;
(e) calculating from image data representing said one or more captured images and from knowledge of the reference radiation a complex field of the collected scattered radiation at the detector;
(f) calculating from the calculated complex field a synthetic radiometric image of radiation diffracted by a periodic structure within the target area.

The invention yet further provides a method of manufacturing devices wherein device features and metrology targets are formed on a series of substrates by a lithographic process, wherein properties of the metrology targets on one or more processed substrates are measured by a method according to the invention as set forth above, and wherein the measured properties are used to adjust parameters of the lithographic process for the processing of further substrates.

The invention yet further provides a computer program product containing one or more sequences of machine-readable instructions for implementing one or more of the calculating steps in a method according to the invention as see forth above.

These and other aspects and advantages of the apparatus and methods disclosed herein will be appreciated from a consideration of the following description and drawings of exemplary embodiments.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 3 (a)-3 (b) illustrates schematically an inspection apparatus adapted to perform a known dark-field imaging inspection methods;

DETAILED DESCRIPTION OF EXEMPLARY EMBODIMENTS

Before describing embodiments of the invention in detail, it is instructive to present an example environment in which embodiments of the present invention may be implemented.

Figure 1:
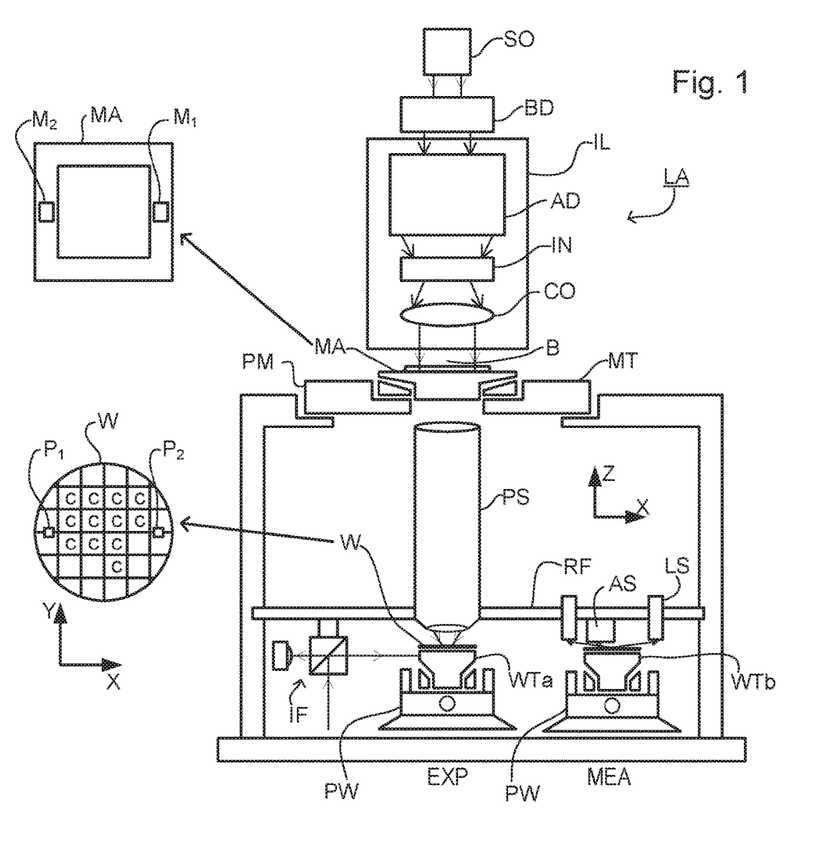
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support MT may be a frame or a table, for example, which may be fixed or movable as required. The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the markers be as small as possible and not require any different imaging or process conditions than adjacent features. The alignment system, which detects the alignment markers is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
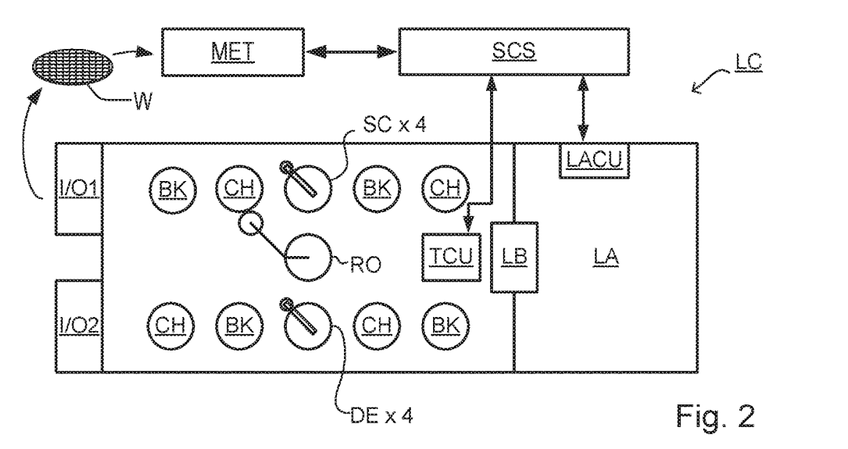
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which lithocell LC is located also includes metrology system MET which receives some or all of the substrates W that have been processed in the lithocell. Metrology results are provided directly or indirectly to the supervisory control system SCS. If errors are detected, adjustments may be made to exposures of subsequent substrates, especially if the inspection can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3A:
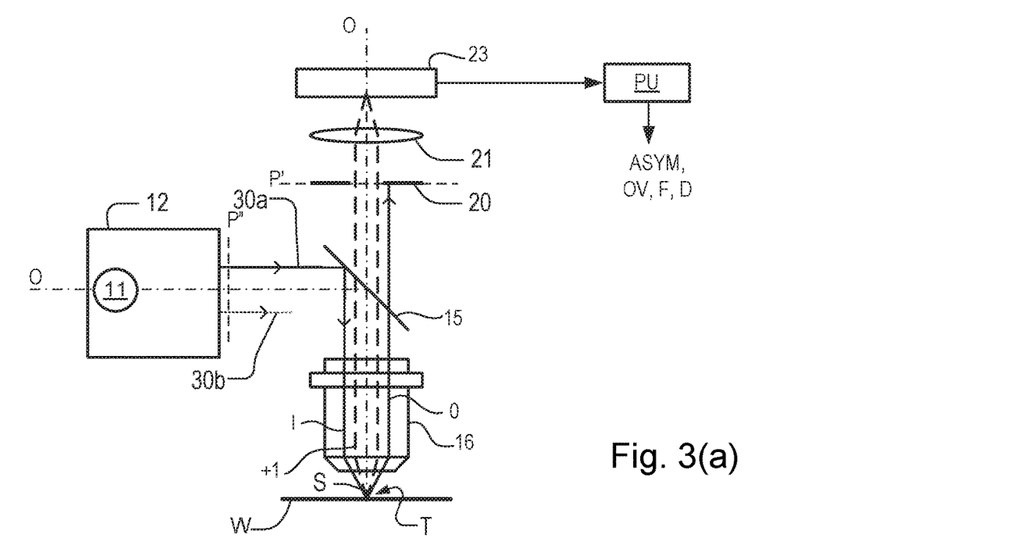

FIG. 3(a) shows schematically the key elements of an inspection apparatus implementing so-called dark field imaging metrology. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating structure T and diffracted rays are illustrated in more detail in FIG. 3(b).

As described in the prior applications cited in the introduction, the dark-filed-imaging apparatus of FIG. 3(a) may be part of a multi-purpose angle-resolved scatterometer that may be used instead of or in addition to a spectroscopic scatterometer. In this type of inspection apparatus, radiation emitted by a radiation source 11 is conditioned by an illumination system 12. For example, illumination system 12 may include a collimating lens system, a color filter, a polarizer and an aperture device. The conditioned radiation follows an illumination path, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired. The multi-purpose scatterometer may have two or more measurement branches. Additionally, further optical systems and branches will be included in a practical apparatus, for example to collect reference radiation for intensity normalization, for coarse imaging of capture targets, for focusing and so forth. Details of these can be found in the prior publications mentioned above. For the purposes of the present disclosure, only the measurement branch of interest for the dark-filed imaging metrology is illustrated and described in detail.

In the collection path for dark-field imaging, imaging optical system 21 forms an image of the target on the substrate W on sensor 23 (e.g. a CCD or CMOS sensor). An aperture stop 20 is provided in a plane P' in the collection path. Plane P' is a plane conjugate to a pupil plane P (not shown) of objective lens 16. Aperture stop 20 may also be called a pupil stop. Aperture stop 20 can take different forms, just as the illumination aperture can take different forms. The aperture stop 20, in combination with the effective aperture of lens 16, determines what portion of the scattered radiation is used to produce the image on sensor 23. Typically, aperture stop 20 functions to block the zeroth order diffracted beam so that the image of the target formed on sensor 23 is formed only from the first order beam(s). In an example where both first order beams are combined to form an image, this would be the so-called dark field image, equivalent to dark-field microscopy. In the present application, however, only one of the first orders is imaged at a time, as explained below. The images captured by sensor 23 are output to image processor and controller PU, the function of which will depend on the particular type of measurements being performed. For the present purpose, measurements of asymmetry of the target structure are performed. Asymmetry measurements can be combined with knowledge of the target structures to obtain measurements of performance parameters of lithographic process used to form them. Performance parameters that can be measured in this way include for example overlay, focus and dose.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. Each of these gratings is an example of a target structure whose properties may be investigated using the inspection apparatus.

The various components of illumination system 12 can be adjustable to implement different metrology 'recipes' within the same apparatus. In addition to selecting wavelength (color) and polarization as characteristics of the particular, illumination system 12 can be adjusted to implement different illumination profiles. Because plane P''' is conjugate with pupil plane P of objective lens 16 and the plane of the detector 19, an illumination profile in plane P''' defines the angular distribution of light incident on substrate W in spot S. To implement different illumination profiles, an aperture device can be provided in the illumination path. The aperture device may comprise different apertures mounted on a movable slide or wheel. It may alternatively comprise a programmable spatial light modulator. As a further alternative, optical fibers may be disposed at different location in the plane P''' and used selectively to deliver light or not deliver light at their respective locations. These variants are all discussed and exemplified in the documents cited above.

In a first example illumination mode, rays 30a are provided so that the angle of incidence is as shown at 'I' and the path of the zero order ray reflected by target T is labeled '0' (not to be confused with optical axis 'O'). In a second illumination mode, rays 30b can be provided, in which case the angles of incidence and reflection will be swapped. Both of these illumination modes will be recognized as off-axis illumination modes. Many different illumination modes can be implemented for different purposes.

Figure 3B:
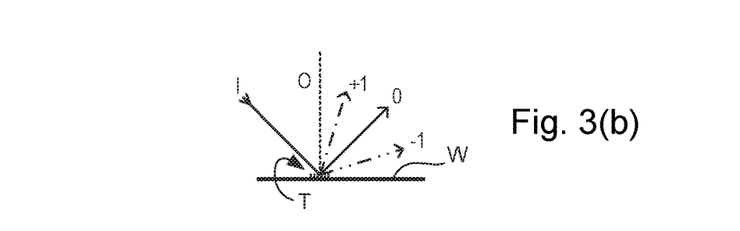

As shown in more detail in FIG. 3(b), target grating T as an example of a target structure is placed with substrate W normal to the optical axis O of objective lens 16. In the case of an off-axis illumination profile, a ray of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the beam of illuminating rays 30a has a finite width (necessary to admit a useful quantity of light), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

Referring also to FIG. 3(a), under the first illumination mode with rays 30a, +1 order diffracted rays from the target grating will enter the objective lens 16 and contribute to the image recorded at sensor 23. When the second illumination mode is used, rays 30b are incident at an angle opposite to rays 30b, and so the −1 order diffracted rays enter the objective and contribute to the image. Aperture stop 20 blocks the zeroth order radiation when using off-axis illumination. As described in the prior publications, illumination modes can be defined with off-axis illumination in X and Y directions.

By comparing images of the target grating under these different illumination modes, asymmetry measurements can be obtained. Alternatively, asymmetry measurements could be obtained by keeping the same illumination mode, but rotating the target. While off-axis illumination is shown, on-axis illumination of the targets may instead be used and a modified, off-axis aperture 20 could be used to pass substantially only one first order of diffracted light to the sensor. In a further example, prisms are used in place of aperture stop 20 which have the effect of diverting the +1 and −1 orders to different locations on sensor 23 so that they can be detected and compared without the need for two sequential image capture steps. This technique, is disclosed in the above-mentioned published patent application US2011102753A1, the contents of which are hereby incorporated by reference. 2nd, 3rd and higher order beams (not shown in FIGS. 3(a)-3(b)) can be used in measurements, instead of or in addition to the first order beams. As a further variation, the off-axis illumination mode can be kept constant, while the target itself is rotated 180 degrees beneath objective lens 16 to capture images using the opposite diffraction orders.

Figure 4:
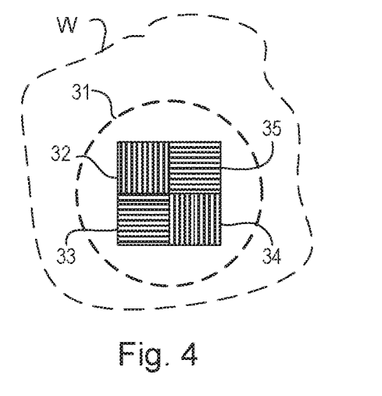
FIG. 4 illustrates a composite metrology target including a number of individual target gratings.

FIG. 4 depicts a composite target formed on a substrate W according to known practice. The composite target comprises four gratings 32 to 35 positioned closely together so that they will all be within the measurement spot S formed by the illumination beam of the metrology apparatus. A circle 31 indicates the extent of spot S on the substrate W. The four targets thus are all simultaneously illuminated and simultaneously imaged on sensor 23. In an example dedicated to overlay measurement, gratings 32 to 35 are themselves composite gratings formed by overlying gratings that are patterned in different layers of the semi-conductor device formed on substrate W. Gratings 32 to 35 may have differently biased overlay offsets in order to facilitate measurement of overlay between the layers in which the different parts of the composite gratings are formed. Gratings 32 to 35 may also differ in their orientation, as shown, so as to diffract incoming radiation in X and Y directions. In one example, gratings 32 and 34 are X-direction gratings with biases of the +d, −d, respectively. This means that grating 32 has its overlying components arranged so that if they were both printed exactly at their nominal locations one of the components would be offset relative to the other by a distance d. Grating 34 has its components arranged so that if perfectly printed there would be an offset of d but in the opposite direction to the first grating and so on. Gratings 33 and 35 are Y-direction gratings with offsets +d and −d respectively. Separate images of these gratings can be identified in the image captured by sensor 23. While four gratings are illustrated, another embodiment might require a larger matrix to obtain the desired accuracy.

Figure 5:
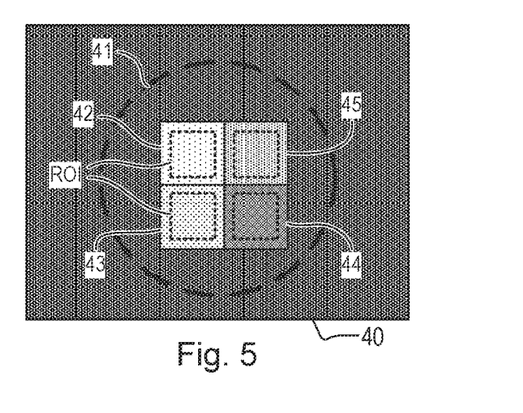
FIG. 5 illustrates an image of the target of FIG. 4, captured by the apparatus of FIG. 4.

FIG. 5 shows an example of an image that may be formed on and detected by the sensor 23, using the target of FIG. 4 in the apparatus of FIGS. 3(a)-3(b), and using an illumination profile providing off-axis illumination in both X and Y orientations simultaneously. The dark rectangle 40 represents the field of the image on the sensor, within which the illuminated spot 31 on the substrate is imaged into a corresponding circular area 41. Within this, rectangular areas 42-45 represent the images of the small target gratings 32 to 35. If the gratings are located in product areas, product features may also be visible in the periphery of this image field. Image processor and controller PU processes these images using pattern recognition to identify the separate images 42 to 45 of gratings 32 to 35. In this way, the images do not have to be aligned very precisely at a specific location within the sensor frame, which greatly improves throughput of the measuring apparatus as a whole. However the need for accurate alignment remains if the imaging process is subject to non-uniformities across the image field. In one embodiment of the invention, four positions P1 to P4 are identified and the gratings are aligned as much as possible with these known positions.

Once the separate images of the gratings have been identified, the intensities of those individual images can be measured, e.g., by averaging or summing selected pixel intensity values within the identified areas. Intensities and/or other properties of the images can be compared with one another to obtain measurements of asymmetry for the four or more gratings simultaneously. These results can be combined with knowledge of the target structures and bias schemes, to measure different parameters of the lithographic process. Overlay performance is an important example of such a parameter, and is a measure of the lateral alignment of two lithographic layers. Overlay can be defined more specifically, for example, as the lateral position difference between the center of the top of a bottom grating and the center of the bottom of a corresponding top-grating. To obtain measurements of other parameters of the lithographic process, different target designs can be used. Again, knowledge of the target designs and bias schemes can be combined with asymmetry measurements to obtain measurements of the desired performance parameter. Target designs are known, for example, for obtaining measurements of dose or focus from asymmetry measurements obtained in this way.

In addition to asymmetry measurements by dark-field imaging of the type described above, measurements of overlay and other parameters can be made by direct imaging of targets.

The amount and accuracy of metrology required in an industry such as semiconductor manufacture is always increasing. The inspection apparatus that will be used as a metrology tool in such an environment should meet many requirements. A large wavelength range may be specified, for example from 300 nm to well beyond 1000 nm. The increasing accuracy requires high-NA optics with low aberrations to allow small in-die targets. Diffraction based measurement using periodic grating structures as targets becomes favored over image-based metrology. The tool should be able to measure very "weak" targets, meaning targets with a low diffraction efficiency due to material absorption in overlying layers. Features of the target structure may be segmented, which further reduces diffraction efficiency of the target. Segmented structures are formed of a collection of smaller sub-structures. The sub-structures are designed to be closer in dimension to product features that are to be formed by the lithographic process under investigation.

Realizing these requirements typically involves significant compromises. For example, high-NA broadband optics with low aberrations leads to many lens elements usually composed of different materials. Each of these elements contributes to internal scattering which limits the detectability of weak targets. Also it becomes increasingly more difficult to have good anti-reflection coatings over a large wavelength range. Having so many optical components leads to an apparatus that is difficult to adjust properly for the metrology application.

Figures 6A, 6B:
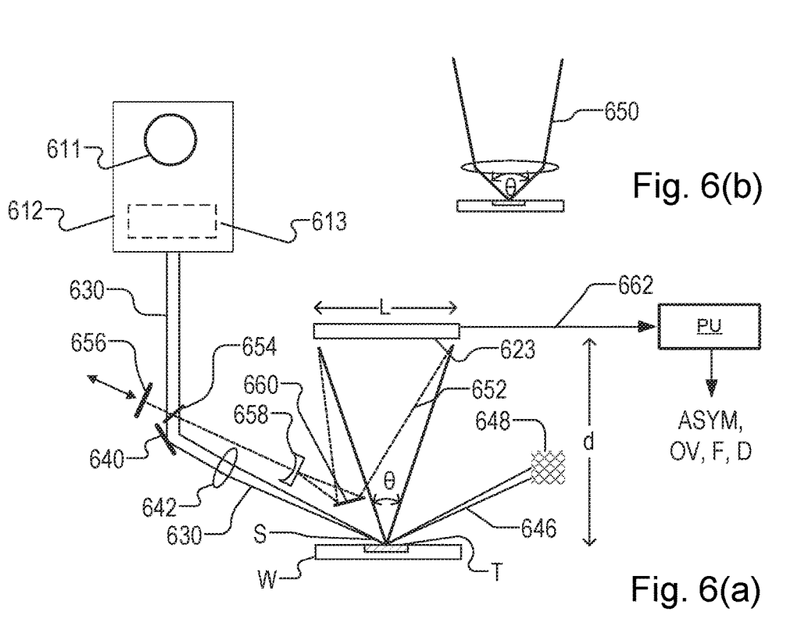
FIGS. 6(a)-6(b) illustrates schematically FIG. 6(a) a modified inspection apparatus according to a first embodiment of the invention, with FIG. 6(b) inset detail of an optional collecting optical system.

FIGS. 6(a)-6(b) shows schematically an inspection apparatus for performing measurements similar to those of FIGS. 3(a), 3(b), 4 and 5, with a simplified optical system. In this apparatus, a modified form of "lensless imaging" or coherent diffractive imaging (CDI) is used. CDI, which is related also to digital holography, is a technique that has been proposed for use in microscopy. In the present disclosure, the CDI technique is adapted to perform metrology on diffractive structures, for example measurement of asymmetry of grating structures. The disclosed apparatus, while not necessarily being completely lensless, avoids the need for the very complicated high-NA, wideband objective lens and other elements, required to meet performance requirements in future applications.

The apparatus of FIG. 6(a) comprises a radiation source 611 and an image sensor 623. Radiation source 611 in this example supplies a beam 630 of spatially coherent radiation, unlike the source 11 in the known apparatus. Source 611 may be formed by one or more narrowband (monochromatic) laser sources, in which case the radiation will be both spatially coherent and temporally coherent. Alternatively, and assumed in the present example, source 611 may be a broadband source which is spatially coherent, with a low temporal coherence. Such a source may be a so-called supercontinuum source or "white light laser". Source 611 may be supplemented with other devices in an illumination system 612 to deliver the beam 630 in a desired form. For example the source 611 and illumination system in some embodiments may include a wavelength selector 613 (shown dotted). Such a wavelength selector may be for example, an acousto-optic tunable filter (AOTF).

Image sensor 623 can be a CCD or CMOS sensor similar to that used for sensor 23 in the existing apparatus. As in the known inspection apparatus, different illumination modes can be implemented by providing an aperture device, a programmable spatial light modulator, or spatially distributed fibers.

In an illumination path from source 611 to target T, an illumination optical system comprises a simple mirror 640 and low-NA lens 642. Lens 642 focuses illuminating radiation beam 630 into a spot S at the location of metrology target T on substrate W. A positioning system (similar for example to the positioning system PW in the lithographic apparatus LA) brings the substrate W and target T to the focal point of beam 630. The spot may be of similar size and shape to the spot in FIGS. 3-5, for example roughly a circle of diameter in the range 10 to 80 μm, for example 20 to 50 μm or around 40 μm. In an embodiment where the illuminating radiation beam 630 is incident at an oblique angle as shown, the spot S may be non-circular, or anamorphic optics can be applied to achieve a circular spot. Radiation 646 reflected by the target (diffracted at zero order) is illustrated for simplicity as being dumped at 648. In a practical embodiment, the reflected (zero order) radiation can be used, for example to determine the focus position of the substrate as part of a position control mechanism. Radiation 650 comprising a desired portion of the radiation scattered by the target T is collected by sensor 623. No high-NA objective lens is required in order to collect the object radiation, and the radiation can pass directly from target to sensor. In a practical example, a simple collection optical system may be provided, for at least roughly collimating the beam (reducing divergence). Such a collection optical system, which may be a simple lens, is shown schematically in the inset diagram at (b). Nevertheless, the complex high-NA objective lens is eliminated. The illuminating radiation can be directed directly at the target area, bypassing the collection optical system. This helps to avoid noise caused by scattering of the illuminating radiation within elements of the optical system.

In addition to the collected scattered radiation 650, reference radiation 652 is also delivered to the sensor 623. The scattered radiation 650 and reference radiation 652 are derived from the same source 611 so as to be coherent with one another and consequently form an interference pattern at the sensor, depending on their relative phases at each pixel on the sensor. In the illustrated example, reference radiation 652 is obtained by splitting off a portion of the illuminating radiation 630 with a beam splitter 654 and delivering it to the sensor via a movable mirror 656, a diverging lens 658 and a folding mirror 660. The reference radiation 650 floods the image sensor 623 with a "reference wave" having a relatively uniform amplitude across the field of sensor 623. The reference wave travels in a direction oblique to an optical axis of the system at a well-defined angle, and so the reference wave has a well-defined amplitude and phase. The scattered radiation 650, which may be referred to as the object wave, has unknown amplitude and phase.

As an alternative to splitting off a portion of the illuminating radiation to form a reference wave, so-called "self-referencing" arrangements are also possible. In that case, a portion the higher order scattered field itself is split off and used as a reference wave. For instance, a self-referencing arrangement may work by interfering a sheared copy of the scattered field with the scattered field.

As will be explained further below, interference between the reference wave and the object wave gives a resulting intensity distribution on the sensor 623 that can be used by processor PU to calculate the complex radiation field of the scattered object wave ("complex" here meaning both amplitude and phase). Image data 662 is delivered to processor PU, representing one or more of these captured intensity distributions. Wave propagation algorithms can then be used to calculate a synthetic image, without the need for imaging optics 21.

Is it not essential that the reference wave is at an oblique angle. However, by using an oblique angle one can introduce a fringe pattern across the target that has a high spatial frequency and can be used to "demodulate" the phase information from a single image acquisition. The angle of the reference wave must not be too large less than the wavelength divided by twice the pixel array pitch lambda/2*pixel size). In a typical set-up, 3-4 degrees may be sufficient, for example. Without this high-frequency fringe pattern, one can obtain the phase information for example by "phase-stepping". As described below, one method for phase stepping is where one acquires multiple images while varying the relative phase of the reference beam. While this can be done, it puts rather severe demands on the stability of the set-up, and the oblique reference beam can therefore be advantageous. In other methods, phase stepping can be done by spatial modulation, such that different phase steps are found within a so-called 'super-pixel'.

Figure 7:
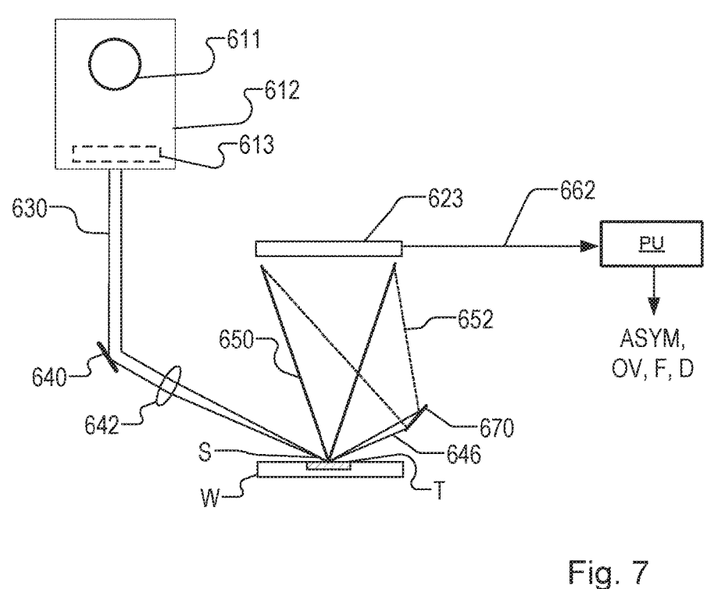
FIG. 7 illustrates schematically a modified inspection apparatus according to a second embodiment of the invention.

The sensor placement and the pitch of its array of pixels should be determined such that the pixel array provides adequate sampling of the interference pattern. As a rough guide, the pixel spacing (pitch) should be less than $\lambda/2d$, where $\lambda$ is the (longest) wavelength in the illuminating radiation 630 and d is the spacing from target T to image sensor 623. In a practical example, the spacing d may be of the order of 1 cm. The sensor dimension may be several times d in each direction (X and Y), for example five or more times d, ten times d or even larger. In this regard, it will be noted that the drawings of FIGS. 6 and 7 are very much distorted in scale, to allow a clear depiction of the optical system. The sensor in practice may be very much closer to the target, or very much wider in extent, than the drawings suggest. For example, the sensor may have a distance d and extent L such that it subtends a relatively wide angle θ when seen from the target T. The angle θ may be over 100 degrees in each dimension, for example over 135 degrees, and for example around 150 degrees. As illustrated in the inset FIG. 6(b), a simple collimating lens 664 can be used to increase the physical distance to the sensor, while still capturing a large range of angles of scattered radiation. The extent of the sensor does not need to be centered over the target as shown. It merely needs to be positioned to capture the desired diffraction orders, based on the angle of incidence of the illuminating radiation, the wavelength(s) of the illuminating radiation and the pitch of the periodic grating.

Variations are possible, for example in the delivery of the reference wave. In the illustrated example, the movable mirror 656 can be used for path length compensation, adjusting the optical path difference between the object wave and the reference wave. If the source 611 is a broadband source such as a white light laser, then stepping with the mirror allows a spectroscopic measurement of the complex radiation field over a large wavelength range. Since the coherence length of a broadband source is relatively small, the apparatus may operate by capturing images while stepping through a wide range of positions. Only some of those positions, corresponding to path length differences close to zero, will be within the coherence length. Other positions will not yield a complex field image. Note that the path length difference may be different at different locations on the sensor, at a given position of the mirror 656. Consequently, each point in the sampled far field will have a maximum fringe contrast at a different position of the mirror. In order to calculate the phase/amplitude for a specific wavelength, one could you would still need to include the information from multiple images in the calculations. In case of low-coherence sources, one will get a contrast variation across the image. This could be calibrated with a test measurement on a test target.

In addition to relaxing design challenges for a given size of image field, the elimination of the complex objective lens allows a larger fields of view to be implemented that would simply be impossible with conventional optics. Instead of a 2×2 array of gratings, for example, a composite target could be imaged with 5×2 or even 5×4 gratings within the field of view.

In order to obtain unambiguous complex radiation field information, the steps of movable mirror 656 can be made much smaller than a (longest) wavelength of the illuminating radiation. In measurement of targets in high-volume manufacturing examples such as semiconductor device manufacturing, the time taken per measurement is critical, but also includes not only the time take for image capture itself but also the time for moving and acquiring each target, prior to image capture. Once the target is acquired, to capture multiple images while stepping the moving mirror 656 may not add significantly to the overall metrology time. The number of steps taken may therefore be quite large in practice, even if many of the captured images contribute little or nothing in the subsequent analysis. Also, if a larger field of view is obtained, more individual gratings or other target structures can be measured in one capture operation.

In other examples, phase stepping can be realized without moving parts such as movable mirror 656. For example, a reflective or transmissive spatial light modulator could be provided with different phase steps at different pixel positions within larger 'superpixels'. Different phase steps could be implemented by etching steps into a suitable material, or by more exotic means. A spatial light modulator based on, for example, liquid crystal, could be used to modulate the phase. In other examples, the wavelength of the reference wave can be varied instead of or in addition to its path length. Provided the wavelength and incidence angle is known, the complex radiation field can be calculated. Wavelength selection can be made by inserting filters in the illumination path, and/or by selecting different radiation sources, or tuning a tunable source.

In other words, phase information can be obtained by varying path length difference with a constant wavelength, by varying wavelength with a constant path length difference, or by a combination of both variations. Wavelength selection can be applied after scattering, if desired. For example wavelength-selecting filters can be inserted in front of image sensor 623 and changed between captures. Multiple image sensors 623 could be provided, with the collection path being split by wavelength-selecting beam splitters. Different pixels within the same image sensor 623 can be made sensitive to different wavelengths, for example in the manner of RGB filter arrays on a single-chip color image sensor.

FIG. 7 shows another variation. Most parts are similar to those illustrated in FIGS. 6 (*a*) and 6(*b*) and the same reference signs are used. The main difference is that the reference radiation 652 is not taken directly from the illuminating radiation 630 but is taken by mirror 670 from the zero order radiation 646 reflected by target T. This variation may or may not simplify the optical layout. A benefit of this variation is that the scattered radiation 650 (object wave) and the reference radiation 652 (reference wave) will be subject to the same influences over a greater portion of their respective optical paths. In particular, any vibrations experience by the target relative to the optical system will influence both the reference wave and the object wave substantially equally. Therefore the influence of these vibrations on the recorded complex field will be reduced. The reference wave in this arrangement will carry some information about the target structure, but this will be only average information, and the reference wave is still effective as a phase reference for the purpose of measuring the complex radiation field of the object wave.

Figure 8:
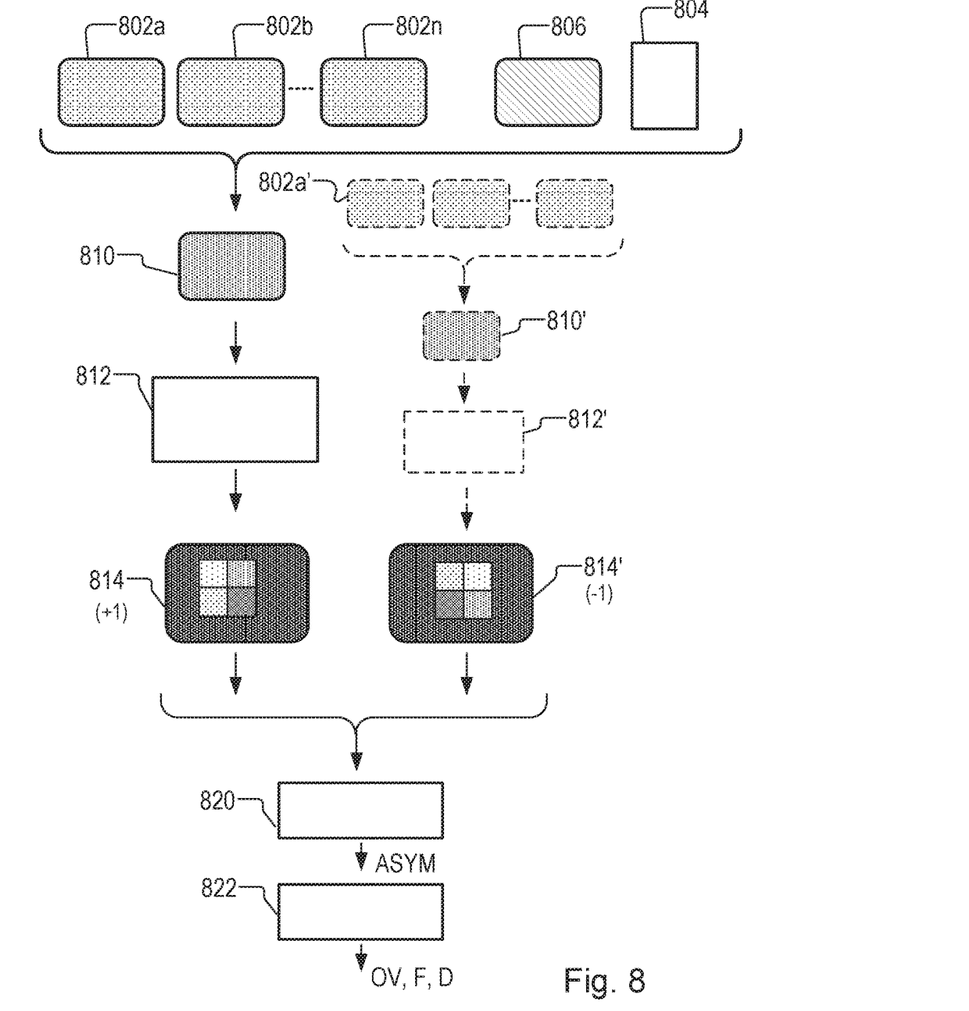
FIG. 8 illustrates a method of measuring properties of a target structure according to an embodiment of the invention, using for example the apparatus of FIG. 6(a), 6(b), 7, 9 or 10.

FIG. 8 illustrates the complete measurement process using the apparatus of FIG. 6(*a*), 6(*b*) or 7. The process is implemented by operation of the optical hardware illustrated in the drawings, in conjunction with processor PU. Functions of (i) controlling the operations of the hardware and (ii) processing the image data 662 may be performed in the same processor, or may be divided between different dedicated processors. Processing of the image data need not even be performed in the same apparatus or even in the same country.

At 802*a*, 802*b*, . . . 802*n* a set of intensity distribution images are captured and received by processor PU from the image sensor 23. Also received is auxiliary data (metadata) 804 defining operating parameters of the apparatus associated with each image, for example the illumination mode, position of mirror 656 and the like. This metadata may be received with each image, or defined and stored in advance for the set of images. The metadata may also include information of the substrate and target structure. Also received or previously stored is reference wave specification 806 defining the known phase of the reference wave as it varies across image sensor 23. The absolute phase does not need to be known as long as you accurately know the relative phase steps across the image sensor, and/or relative to an arbitrary initial position of the movable mirror. Additional calibration procedures can be provided to obtain this information, rather than relying on design and calculation alone.

From the received image data 802*a* etc., the metadata 804 and the reference wave specification 806, processor PU calculates a complex radiation field 810. This is a representation of amplitude and phase of the object wave (scattered radiation 650) across the image sensor 23. The representation may be expressed in the form of amplitude and phase values per pixel position. Other equivalent forms of expression are also available. From this complex radiation field, processor PU in a process 812 can use wave propagation algorithms to calculate a synthetic image 814 as it would be seen if focused by an ideal optical system onto an image sensor (similar to sensor 23 of FIGS. 3(*a*)-3(*b*)).

As illustrated schematically in FIG. 8, synthetic image 814 can have the same form as the real image shown in FIG. 5. Dark and light rectangles corresponding to each individual grating in a composite target are shown, just by way of example. The synthetic image may be an image of intensity, analogous to the real images captured in the known apparatus. However, the synthetic image does not necessarily have to be an intensity image. It can also be a phase image of the grating, or both intensity/amplitude and phase images can be calculated. As already discussed above, two such images can be used to calculate asymmetry of each grating, if the two images are produced using opposite portions of a diffraction spectrum of the target. In FIG. 8 a second synthetic image 814' is shown. It will be understood that the second synthetic image is obtained by the same process as image 814, based on a second set of images 802*a'*, etc. that are captured using image sensor 623 when the illumination profile or orientation of the target has been rotated 180 degrees. In other words, the synthetic image 814 is be produced using (for example)+1 order diffracted radiation, while synthetic image 814' is produced using −1 order diffracted radiation.

At step 820 processor PU compares intensities of the images of different gratings in the images 814 and 814' to obtain asymmetry measurements of each grating. At step 822 the measured asymmetries of the multiple gratings within composite target are converted by a predetermined formula and/or calibration curves to obtain a measurement of a parameter of interest, such as overlay OV, focus F or dose D. The formulae are derived from knowledge of the target structures, including the bias scheme applied. Calibration curves may be obtained by comparing asymmetry measurements on a range of targets with measurements of the parameter of interest made by other techniques such as electron microscopy (SEM, TEM).

The illustrated process is repeated for all targets of interest. Note that the computational parts of the process can be separated in time and space from the image capture. The computations do not need to be completed in real time, although of course that would be desirable. Only the capturing of the images need 802*a* etc. requires the presence of the substrate, and so impacts productivity throughput) of the lithographic device manufacturing process overall.

As mentioned above, the number of images 802*a* captured may be greater than the number selected and used to calculate the complex radiation field. The number used can be selected according to requirements. In principle, four images captured with different (known) phase steps between the object wave and the reference wave should be sufficient to obtain unambiguous amplitude and phase information. Alternatively, four images captured with different (known) wavelengths of illuminating radiation 630 would be sufficient. Greater numbers can be used to improve measurement certainty. The number of images required for the calculation may be reduced if the calculation can be constrained using knowledge of the target structure and substrate. Phase stepping algorithms are known which are proven to be more robust to noise. For example five-step phase shifting algorithms are more robust to phase shifter calibrations. Multi-step algorithms exist which do not require the knowledge of the phase step as long it is identical. Random phase step algorithms also exist. See for example, James C Wyant, "Phase Shifting Interferometry.nb.pdf", Optics 513 Chapter 5, Chapter Notes, 2011 available at http://fp.optics.arizona.edu/jcwyant/Optics513/ChapterNotes/Chapter05/Notes/Phase %20 Shifting %20Interferometry.nb.pdf.

In the above examples the steps of calculating the complex field 810 and calculating the synthetic image 814 are shown as separated sequentially. This is likely to be a convenient way to proceed in practice. In principle, however, the calculations could be merged so that one proceeds by a single calculation directly from the captured images 802$a$ etc. to the synthetic image 814, without explicitly calculating the complex field. The claims should not be interpreted as requiring explicit calculation of the complex field as a distinct array of data.

In addition to calculating synthetic images of the target as it would be seen by image sensor 23 of the known dark-field imaging scatterometer, the apparatus can calculate synthetic images of the diffraction pattern as it would be seen in a pupil image sensor. Unlike the known apparatus, no splitting of the collected radiation into different optical branches is required to obtain these different images.

Figure 9:
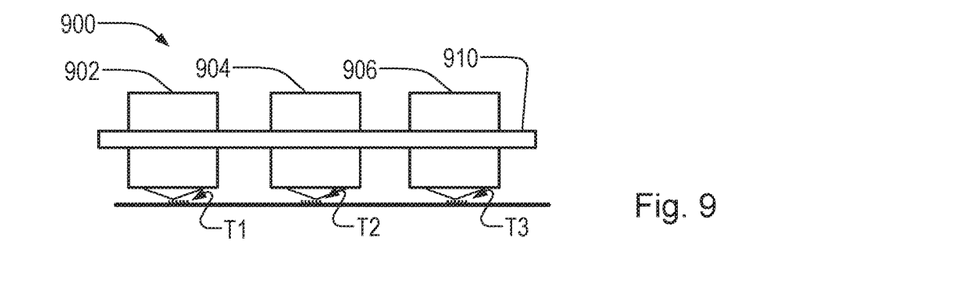
FIG. 9 illustrates a fourth embodiment of an inspection apparatus for measuring properties of multiple targets in parallel.

FIG. 9 illustrates an inspection apparatus 900 in which a number of targets can be measured in parallel. In the example, three optical systems 902, 904, 906 are mounted on a supporting structure 910. Each optical system comprises an inspection apparatus of the type shown in FIGS. 6($a$), 6($b$) and 7. As will be appreciated, with appropriate spacing of the optical systems and targets on the substrate, multiple targets T1, T2, T3 can be captured simultaneously. The fact that the images 814 etc. are computed from complex radiation field data in a step that is distinct from the step of physical image capture means that many design constraints can be relaxed. Some of these more relaxed constraints are discussed above. In the parallel implementation of FIG. 9, the large field of view and calculated focusing of the synthetic images allow a wide margin for capturing several targets simultaneously in X, Y and Z (focus) directions.

Conclusion

The inspection apparatuses disclosed herein enable improvements in the field of view and bandwidth of the measurement optical system without an associated increase in complexity and cost of the objective lens and other components. A very large wavelength range can be covered with very simple optics. From an application point of view this large wavelength range is highly desirable to improve the accuracy of measurements and to be robust against particular processes that make measurement at particular known wavelengths difficult. Multiple CCD's or similar image sensors 623 can optionally be used to cover a range of wavelengths from say 300 nm to 1500 nm or more.

Coherent mixing of the object wave with a reference wave derived directly from the source or from a reflected zeroth order also provides optical amplification ("homodyning") which ensures a large dynamic range and the capability to detect very low contrast gratings. In "self-referenced" embodiments, on the other hand, the reference wave may be a modified copy of the scattered radiation 650. Benefits of self-referenced embodiments may be for example the stability of the signal, since the reference is derived from the measurement signal.

The "Optics", so far as there is any, is completely achromatic and very tolerant for focus errors since the entire image formation is done computationally. This focus tolerance is important for example in allowing the regions of interest (ROI, FIG. 5) to be defined to include exactly the same portion of the target in the two images being compared. As seen in FIG. 10 below, it may also be useful to allow capture of images from several targets in parallel, without focusing each target individually at the time of capture.

Since the image sensor 623 is on a 'Fourier-like' plane, the effect of localized noise (like dust, dead pixels) is spread out over all the pixels in the synthetic image and has a lesser impact on the computed image. (As opposed to direct imaging on a CCD or like sensor).

A method of manufacturing devices using the lithographic process can be improved by providing an inspection apparatus as disclosed herein, using it to measure processed substrates to measure parameters of performance of the lithographic process, and adjusting parameters of the process to improve or maintain performance of the lithographic process for the processing of subsequent substrates.

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed.

In association with the optical system hardware, an embodiment may include a computer program containing one or more sequences of machine-readable instructions defining methods of calculating synthetic images and/or controlling the inspection apparatus to implement the illumination modes and other aspects of those metrology recipes. This computer program may be executed for example in a separate computer system employed for the image calculation/control process. Alternatively, the calculation steps may be wholly or partly performed within unit PU in the apparatus of FIGS. 6($a$), 6($b$) and 7, or 9 and/or the control unit LACU of FIG. 2. There may also be provided a data storage medium (e.g., semiconductor memory, magnetic or optical disk) having such a computer program stored therein.

Further embodiments according to the invention are provided in below numbered clauses:

1. An inspection apparatus for measuring properties of a target structure, the apparatus comprising a radiation source and an image detector in combination with an optical system, the optical system defining the following beam paths:
   an illumination path for receiving radiation from the radiation source, forming a beam of spatially coherent illuminating radiation and delivering said illuminating radiation onto a target area on a substrate;

a collection path for collecting at least a portion of non-zero order scattered radiation from said target area and delivering the collected scattered radiation to the image detector; and a reference path for delivering reference radiation to the image detector, wherein the reference radiation is coherent with the scattered radiation so as to interfere with the scattered radiation and form an interference pattern at the image detector, wherein the image detector is configured to capture one or more images of said interference pattern, and wherein the inspection apparatus further comprises a processor arranged (i) to receive image data representing said one or more captured images, (ii) to calculate from the image data and from knowledge of the reference radiation a complex field of the scattered radiation at the detector, (iii) to calculate from the complex field a synthetic radiometric image of radiation diffracted by a periodic structure within the target area.

2. An inspection apparatus according to clause 1 wherein said reference path includes the target area of the substrate, the reference radiation being obtained from a portion of the scattered radiation.

3. An inspection apparatus according to clause 2 wherein the reference radiation is obtained from a zero order portion of the scattered radiation.

4. An inspection apparatus according to clause 2 wherein the reference radiation is obtained from a non-zero order portion of the scattered radiation.

5. An inspection apparatus according to any preceding clauses wherein one or both of said illumination path and said reference path includes a moveable element for adjusting an optical path difference between the scattered radiation and the reference radiation where they interfere at the image detector.

6. An inspection apparatus according to clause 5 wherein said processor is configured to calculate said complex field from images of the interference pattern captured with different optical path differences.

7. An inspection apparatus according to clause 6 wherein said illuminating radiation is broadband illumination and the processor is configured to calculate said complex field from one or more images of the interference pattern captured with optical path difference(s) of less than a coherence length of the broadband radiation.

8. An inspection apparatus according to any preceding clauses including a wavelength selector for selecting a wavelength of said illuminating radiation.

9. An inspection apparatus according to clause 8 wherein said processor is configured to calculate said complex field from images of the interference pattern captured with different wavelengths.

10. An inspection apparatus according to any preceding clauses wherein said collection path includes one or more elements for reducing divergence of the scattered radiation at the detector.

11. An inspection apparatus according to any preceding clauses wherein said complex field is calculated also using information defining known properties of a target structure.

12. An inspection apparatus according to clause 11 wherein the processor is arranged to extract from said synthetic radiometric image information relating to a plurality of individual target structures within the same target area, each target structure being represented at a different region within said synthetic radiometric image.

13. An inspection apparatus according to any preceding clauses wherein processor is further configured to calculate a property of one or more target structure by combining information from synthetic radiometric images calculated from image data representing of the same target area captured under different conditions.

14. An inspection apparatus according to clause 13 wherein said property is asymmetry, the collected scattered radiation under the different conditions comprising opposite portions of a diffraction spectrum of a target structure.

15. An inspection apparatus according to clause 13 or 14 wherein the processor is further arranged (iv) to repeat steps (i) to (iii) under different conditions and calculate at least one further synthetic radiometric image of the same target area and (v) to calculate from the plurality of synthetic radiometric images a measure of asymmetry in the target structure 16. An inspection apparatus according to clause 14 or 15 wherein the processor is configured to calculate measurements of asymmetry for multiple target structures, and wherein said processor is further arranged to calculate using said measurements and known characteristics of the multiple target structures a performance parameter of a lithographic process used to form the target structures.

17. An inspection apparatus according to clause 16 wherein said performance parameter of the lithographic process is one of overlay, focus and dose.

18. An inspection apparatus according to clause 16 or 17 wherein the processor is arranged to extract information relating to said multiple target structures from the same captured images, each target structure being represented at a different region in said synthetic image.

19. An inspection apparatus according to any preceding clauses wherein a plurality of optical systems and image detectors are provided for capturing images of interference patterns from multiple target areas in parallel.

20. An inspection apparatus according to any preceding clauses wherein the processor is further configured to calculate a synthetic diffraction pattern representing one or more selected portions of the diffraction spectrum of the target.

21. A method for measuring properties of a target structure, the method comprising the steps:
(a) illuminating a target area on a substrate with spatially coherent illuminating radiation;
(b) collecting at least a portion of non-zero order scattered radiation from said target area and delivering the collected scattered radiation to the image detector;
(c) delivering a beam of reference radiation to the image detector the reference radiation being coherent with the scattered radiation so as to interfere with the collected scattered radiation and form an interference pattern at the image detector;
(d) capturing with the image detector one or more images of said interference pattern;
(e) calculating from image data representing said one or more captured images and from knowledge of the reference radiation a complex field of the collected scattered radiation at the detector;
(f) calculating from the calculated complex field a synthetic radiometric image of radiation diffracted by a periodic structure within the target area.

22. A method according to clause 21 wherein the reference radiation is obtained from radiation scattered by the target area.

23. A method according to clause 22 wherein the reference radiation is obtained from zero order radiation scattered by the target area.

24. A method according to clause 22 wherein the reference radiation is obtained from non-zero order radiation scattered by the target area.

25. A method according to any of clauses 21 to 24 further including adjusting an optical path difference between the scattered radiation and the reference radiation where they interfere at the image detector.

26. A method according to clause 25 wherein step (e) comprises calculating said complex field from images of the interference pattern captured with different optical path differences.

27. A method according to clause 26 wherein said illuminating radiation is broadband illumination and step (e) comprises calculating said complex field from one or more images of the interference pattern captured with optical path difference(s) of less than a coherence length of the broadband radiation.

28. A method according to any of clauses 21 to 27 wherein a wavelength selector is used to select a wavelength of said illuminating radiation.

29. A method according to clause 28 wherein step (e) comprises calculating said complex field from images of the interference pattern captured with different wavelengths.

30. A method according to any of clauses 21 to 29 wherein said collection step (b) uses one or more elements for reducing divergence of the scattered radiation at the detector.

31. A method according to any of clauses 21 to 30 wherein in step (e) said complex field is calculated also using information defining known properties of a target structure.

32. A method according to clause 31 wherein step (f) comprises extracting from said synthetic radiometric image information relating to a plurality of individual target structures within the same target area, each target structure being represented at a different region within said synthetic radiometric image.

33. A method according to any of clauses 21 to 32 further comprising the steps:
 (g) repeating steps (a) to (f) under different conditions to calculate at least one further synthetic radiometric image of the same target area, the collected scattered radiation under the different conditions comprising opposite portions of a diffraction spectrum of a target structure; and
 (h) calculating from the plurality of synthetic radiometric images a measure of asymmetry in the target structure.

34. A method according to clause 33 wherein the processor is configured to calculate measurements of asymmetry for multiple target structures, and wherein said processor is further arranged to calculate using said measurements and known characteristics of the multiple target structures a performance parameter of a lithographic process used to form the target structures.

35. A method of manufacturing devices wherein device features and metrology targets are formed on a series of substrates by a lithographic process, wherein properties of the metrology targets on one or more processed substrates are measured by a method according to any of clauses 21 to 34, and wherein the measured properties are used to adjust parameters of the lithographic process for the processing of further substrates.

36. A computer program product containing one or more sequences of machine-readable instructions for implementing the step (e) of a method of any of clauses 21 to 34.

37. A computer program product containing one or more sequences of machine-readable instructions for implementing the steps (e) and (f) of a method of any of clauses 21 to 34.

38. A computer program product containing one or more sequences of machine-readable instructions for implementing the steps (e), (f) and (h) of a method of any of clauses 33 and 34.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An inspection apparatus for measuring properties of a target structure, the apparatus comprising:
 a radiation source; and
 an image detector in combination with an optical system, the optical system defining the following beam paths:
  an illumination path for receiving radiation from the radiation source, forming a beam of spatially coherent illuminating radiation and delivering said illuminating radiation onto a target area on a substrate;
  a collection path for collecting at least a portion of non-zero order scattered radiation from said target area and delivering the collected scattered radiation to the image detector; and
  a reference path for delivering reference radiation to the image detector,
 wherein the reference radiation is coherent with the scattered radiation so as to interfere with the scattered radiation and form an interference pattern at the image detector, wherein the image detector is configured to capture one or more images of said interference pattern, and a processor arranged (i) to receive image data representing said one or more captured images, (ii) to calculate from the image data and from knowledge of the reference radiation a complex field of the scattered radiation at the detector, (iii) to calculate from the complex field a synthetic radiometric image of radiation diffracted by a periodic structure within the target area.

2. An inspection apparatus as claimed in claim 1 wherein one or both of said illumination path and said reference path includes a moveable element for adjusting an optical path difference between the scattered radiation and the reference radiation where they interfere at the image detector.

3. The inspection apparatus as claimed in claim 2 wherein said processor is configured to calculate said complex field from images of the interference pattern captured with different optical path differences.

4. The inspection apparatus as claimed in claim 3 wherein said illuminating radiation is broadband illumination and the processor is configured to calculate said complex field from one or more images of the interference pattern captured with optical path difference(s) of less than a coherence length of the broadband radiation.

5. The inspection apparatus as claimed in claim 1 wherein the processor is arranged to extract from said synthetic radiometric image information relating to a plurality of individual target structures within the same target area, each target structure being represented at a different region within said synthetic radiometric image.

6. The inspection apparatus as claimed in claim 1 wherein processor is further configured to calculate a property of one or more target structure by combining information from synthetic radiometric images calculated from image data representing of the same target area captured under different conditions.

7. The inspection apparatus as claimed in claim 6 wherein said property is asymmetry, the collected scattered radiation under the different conditions comprising opposite portions of a diffraction spectrum of a target structure.

8. The inspection apparatus as claimed in claim 6 wherein the processor is further arranged (iv) to repeat (i) to (iii) under different conditions and calculate at least one further synthetic radiometric image of the same target area and (v) to calculate from the plurality of synthetic radiometric images a measure of asymmetry in the target structure.

9. A method for measuring properties of a target structure, the method comprising:
illuminating a target area on a substrate with spatially coherent illuminating radiation;
collecting at least a portion of non-zero order scattered radiation from said target area and delivering the collected scattered radiation to the image detector;
delivering a beam of reference radiation to the image detector the reference radiation being coherent with the scattered radiation so as to interfere with the collected scattered radiation and form an interference pattern at the image detector;
capturing with the image detector one or more images of said interference pattern;
calculating from image data representing said one or more captured images and from knowledge of the reference radiation a complex field of the collected scattered radiation at the detector; and
calculating from the calculated complex field a synthetic radiometric image of radiation diffracted by a periodic structure within the target area.

10. The method as claimed in claim 9 further including adjusting an optical path difference between the scattered radiation and the reference radiation where they interfere at the image detector.

11. A method as claimed in claim 10 wherein the calculating from the image data comprises calculating said complex field from images of the interference pattern captured with different optical path differences.

12. The method as claimed in claim 11 wherein:
said illuminating radiation is broadband illumination; and
the calculating from image data comprises calculating said complex field from one or more images of the interference pattern captured with optical path difference(s) of less than a coherence length of the broadband radiation.

13. The method as claimed in claim 9 wherein a wavelength selector is used to select a wavelength of said illuminating radiation.

14. The method as claimed in claim 9 wherein said collecting uses one or more elements for reducing divergence of the scattered radiation at the detector.

15. The method as claimed in claim 9 wherein said complex field calculated from the image data is calculated also using information defining known properties of a target structure.

16. The method as claimed in claim 15 wherein the calculating from the calculated complex field comprises extracting from said synthetic radiometric image information relating to a plurality of individual target structures within the same target area, each target structure being represented at a different region within said synthetic radiometric image.

17. A method as claimed in claim 9 further comprising:
repeating the illuminating, collecting, delivering, capturing, and calculating under different conditions to calculate at least one further synthetic radiometric image of the same target area, the collected scattered radiation under the different conditions comprising opposite portions of a diffraction spectrum of a target structure; and
calculating from the plurality of synthetic radiometric images a measure of asymmetry in the target structure.

18. The method as claimed in claim 17 wherein the processor is configured to calculate measurements of asymmetry for multiple target structures, and wherein said processor is further arranged to calculate using said measurements and known characteristics of the multiple target structures a performance parameter of a lithographic process used to form the target structures.

19. A method of manufacturing devices comprising:
forming device features and metrology targets on a series of substrates by a lithographic process,
measuring properties of a target structure comprising:
illuminating a target area on a substrate with spatially coherent illuminating radiation;
collecting at least a portion of non-zero order scattered radiation from said target area and delivering the collected scattered radiation to the image detector;
delivering a beam of reference radiation to the image detector the reference radiation being coherent with the scattered radiation so as to interfere with the collected scattered radiation and form an interference pattern at the image detector;
capturing with the image detector one or more images of said interference pattern;
calculating from image data representing said one or more captured images and from knowledge of the reference radiation a complex field of the collected scattered radiation at the detector; and calculating from the calculated complex field a synthetic radiometric image of radiation diffracted by a periodic structure within the target area measuring, wherein the measured properties are used to adjust parameters of the lithographic process for the processing of further substrates.

\* \* \* \* \*